(12) United States Patent
Slavin

(10) Patent No.: US 6,544,787 B1
(45) Date of Patent: Apr. 8, 2003

(54) NON-MYELOABLATIVE/LYMPHOABLATIVE CONDITIONING REGIMEN TO INDUCE PATIENT ANTI-DONOR UNRESPONSIVENESS IN STEM CELL TRANSPLANTATION

(75) Inventor: Shimon Slavin, Jerusalem (IL)

(73) Assignees: Hadash Medical Research Services and Development Ltd., Jerusalem (IL); Baxter International Inc., Deerfield, IL (US)

( * ) Notice: Subject to any disclaimer, the term of this patent is extended or adjusted under 35 U.S.C. 154(b) by 0 days.

(21) Appl. No.: 08/995,049

(22) Filed: Nov. 14, 1997

Related U.S. Application Data
(60) Provisional application No. 60/037,024, filed on Jan. 30, 1997, and provisional application No. 60/030,833, filed on Nov. 15, 1996.

(51) Int. Cl.⁷ .................................................. C12H 5/08
(52) U.S. Cl. ................... 435/372; 424/93.71; 435/7.24; 435/325; 435/372.3; 435/372.2; 435/375
(58) Field of Search ................................. 435/372, 366, 435/372.3, 93.7, 93.71

(56) References Cited

U.S. PATENT DOCUMENTS

| | | | |
|---|---|---|---|
| 5,004,681 A | 4/1991 | Boyse et al. | 435/2 |
| 5,514,364 A | 5/1996 | Ildstad | 424/1.49 |
| 5,635,156 A | 6/1997 | Ildstad | 424/1.49 |

FOREIGN PATENT DOCUMENTS

WO    WO 95/24910    9/1995

OTHER PUBLICATIONS

W.I. Bensinger, et al., "Transplantation of Allogeneic Peripheral Blood Stem Cells Mobilized by Recombinant Human Granulocyte Colony–Stimulating Factor," *Blood*, 85: 1655–1658 (1995).

P.J. Henslee–Downey, et al., "Minimal Risk of Graft Versus Host Disease (GVHD) Following Haploidentical But Partially Mismatched Related Donar (PMRD) Bone Marrow Transplantation," 23rd Annual Meeting, International Society For Experimental Hematology, Minneapolis, Minnesota, Abstract 147 (1994).

C.L. Kaufman, et al., "Phenotypic Characterization of a Novel Bone Marrow–Derived Cell That Faciliatates Engraftment of Allogeneic Bone Marrow Stem Cells," *Blood*, 84: 2436–2446 (1994).

M. Korbling, et al., "Allogeneic Blood Stem Cell Transplantation for Refractory Leukemia and Lymphoma: Potential Advantage of Blood Over Marrow Allografts," *Blood*, 85: 1659–1665 (1995).

S. Mackinnon, et al., "Adoptive Immunotherapy Evaluating Escalating Doses of Donor Leukocytes for Relapse of Chronic Myeloid Leukemia After Bone Marrow Transplantation: Separation of Graft–Versus–Leukemia Responses From Graft–Versus–Host Disease," *Blood*, 86: 1261–1268 (1995).

*Primary Examiner*—Laurie Scheiner
*Assistant Examiner*—Jeffrey S. Parkin
(74) *Attorney, Agent, or Firm*—G. E. Ehrlich Ltd.

(57) ABSTRACT

Serious hematologic malignancies are treated through high dose or lethal chemotherapy and/or radiation therapy conditioning regimens followed by rescue with allogeneic stem cell transplantation (allo-SCT) or autologous stem cell transplantation (ASCT). These myeloablative/lymphoablative (M/L) treatment regimens involve the elimination of both the patient's hematopoietic stem cells and T-lymphocytes, often leading to serious complications including graft versus host disease (GVHD). The claimed invention addresses some of these problems by providing a conditioning regimen that is designed to eliminate the patient's T-lymphocytes while retaining a functional population of hematopoietic stem cells (HSC). This non-myeloablative/lymphoablative (-/L) conditioning regimen involves the administration of one or more agents such as purine analogs (e.g., fludarabine), alkylating agents (e.g., bisulfan, cyclophosphamide), or anti-leukocyte globulins (e.g., anti-T lymphocyte globulin). After this, a donor-derived allogeneic stem cell preparation is administered to the patient. Patients treated according to the claimed invention develop donor-specific unresponsiveness and relatively fewer complications as compared to standard M/L conditioning regimens. The claimed methodologies should prove useful in the treatment of a number of hematologic malignancies such as chronic myelogenous leukemia, acute myelogenous leukemia, acute lymphoblastic leukemia, and non-Hodgkin's lymphoma.

27 Claims, 3 Drawing Sheets

NON-MYELOABLATIVE/LYMPHOABLATIVE CONDITIONING REGIMEN TO INDUCE PATIENT ANTI-DONOR UNRESPONSIVENESS IN STEM CELL TRANSPLANTATION

This application claims priority from U.S. provisional application Ser. No. 60/030,833, filed Nov. 15, 1996 and U.S. provisional application Serial No. 60/037,024, filed Jan. 30, 1997.

BACKGROUND OF THE INVENTION

High dose or lethal conditioning regimens using chemotherapy and/or radiation therapy followed by rescue with allogeneic stem cell transplantation (allo-SCT) or autologous stem cell transplantation (ASCT) have been the treatments of choice for patients with a variety of hematologic malignancies and chemosensitive solid tumors resistant to conventional doses of chemotherapy. A common source of stem cells for such procedures has been the bone marrow. Recently, peripheral blood stem cells (PBSC) have also been used. As such, the terms "allogeneic bone marrow transplantation" (allo-BMT) and "autologous bone marrow transplantation" (ABMT) are widely used in the literature to refer to particular types of allo-SCT and ASCT, respectively, whether the rescue is with bone marrow or PBSC.

Current procedures typically employ allo-SCT or ASCT after myeloablative/lymphoablative (M/L) conditioning. As the name implies, M/L conditioning involves elimination, through cell killing, blocking, and/or down-regulation, of substantially all the hematopoietic stem cells and lymphocytes of the patient. Patients treated by allo-SCT or ASCT can develop major complications due to the M/L conditioning. In addition, patients receiving allo-SCT are susceptible to graft versus host disease (GVHD), as well as to graft rejection. Moreover, relapse is still a frequent problem in these patients.

Several attempts to improve disease-free survival by increasing the intensity of the M/L conditioning have failed due to unacceptable toxicity. Furthermore, increasing the intensity of the M/L conditioning does not appear to improve the outcome by decreasing the rate of relapse. A wide variety of protocols of varying intensities have been used among greater than 30,000 transplants worldwide reported to the International Bone Marrow Transplant Registry. Despite these numerous attempts to vary the intensity of the conditioning regimens, there have not been any documented significant differences in the over-all patient outcomes.

The use of M/L conditioning followed by rescue with allo-SCT is often accompanied by graft-versus-tumor (GVT), for example, graft-versus-leukemia (GVL), responses. Over the years, immune interactions between allogeneic donor-derived immunocompetent T lymphocytes acting against host-type tumor cells have been shown to be of major therapeutic importance. For example, significantly better anti-tumor effects have been induced by allo-SCT as compared with ASCT or transplants from an identical twin.

Relapse following allo-SCT or ASCT in patients has sometimes been reversed by adoptive allogeneic cell therapy (allo-CT) using donor lymphocyte infusions (DLI). Complete eradication of tumor cells by DLI, despite resistance of the tumor cells to maximally tolerated doses of M/L conditioning, suggests that alloreactive T lymphocytes may represent a crucial weapon against tumor cells. Allogeneic stem cell transplantation leading to engraftment of allogeneic stem cells in the host may function merely to induce a state of host-versus-graft tolerance, allowing concomitantly or subsequently administered allogeneic donor-derived T lymphocytes to survive and to recognize and eradicate host-derived tumor cells.

In fact, the main therapeutic component of allo-SCT may be ascribed to T lymphocyte mediated GVT or GVL effects rather than to physical elimination of tumor cells by the M/L conditioning prior to transplantation. GVL or GVT effects mediated by T lymphocytes generally occur in the context of allo-SCT, allogeneic peripheral blood stem cell transplantation (allo-PBSCT; i.e., one form of allo-SCT) or allo-CT. However, as discussed above, these procedures can lead to complications related to the M/L conditioning, GVHD, and/or graft rejection.

SUMMARY OF THE INVENTION

This invention provides for new methods of treating a human patient with a pathogenic cell disease. It has been discovered that conditioning regimens can be designed that allow the patient to retain relatively high levels of either stem cells or functional lymphocytes. Thus, in one method, the conditioning regimen is designed to eliminate the patient's T lymphocytes but to allow retention of a functional population of the patient's hematopoietic stem cells. In a second method, the conditioning regimen is designed to ablate the patient's stem cells but to allow retention of a functional population of the patient's lymphocytes. In both methods, after the patient has been treated with the conditioning regimen, a donor-derived allogeneic stem cell preparation is administered to the patient.

Patients treated according to the methods of the invention develop donor-specific unresponsiveness and also develop relatively fewer complications than with the standard M/L regimens. The method also provides a platform for performing allo-CT for inducing GVL, GVT or graft versus autoimmunity (GVA) effects, and allows for development of patient-specific allogeneic stem cell preparations.

In a first aspect, the invention features a method of treating a human patient having a pathogenic cell disease. The method includes treating the patient with a conditioning regimen that retains a functional population of the patient's hematopoietic stem cells. The method also involves administering a preparation that includes allogeneic stem cells from a donor to the patient under conditions effective for inducing host anti-donor unresponsiveness. The regimen can be a m/L conditioning regimen or a -/L conditioning regimen. Preferably, the allogeneic stem cells are peripheral blood stem cells, cord blood stem cells or bone marrow stem cells.

The method may also include a step of providing allogeneic cell therapy to the patient. The allogeneic cell therapy is provided following induction of host anti-donor unresponsiveness and in the absence of significant GVHD. The allogeneic cell therapy can include administration of donor T lymphocytes in graded increments while controlling for GVHD without immunosuppression. The T lymphocytes may be lifespan-limited. The T lymphocytes may be CD8+ cells or CD4+ cells. In one embodiment, allogeneic cell therapy may include administration of donor T lymphocytes activated in vitro, prior to administration, to the patient. In another embodiment, allogeneic cell therapy may include in vivo administration of T cell activator to the patient.

The conditioning regimen can include administration of one or more agents such as purine analogs, alkylating agents or anti-leukocyte globulins. In one embodiment, the purine analog is fludarabine and the anti-leukocyte globulin is anti-T lymphocyte globulin.

In another embodiment, the regimen includes administration of fludarabine, anti-T lymphocyte globulin and an alkylating agent. The alkylating agent may be, for example, busulfan or cyclophosphamide.

Pathogenic cell diseases treatable with the methods include malignant diseases such as chronic myelogenous leukemia, acute myelogenous leukemia, acute lymphoblastic leukemia, non-Hodgkin's lymphoma, myelodysplastic syndrome or multiple myeloma. The malignant disease may also be a solid tumor as in metastatic breast cancer.

In another embodiment, the pathogenic cell disease can be a non-malignant diseases such as β-thalassemia major, Blackfan Diamond Anemia, Gaucher's anemia, Fanconi's anemia or AIDS. The non-malignant disease may also be an autoimmune disease.

In a second aspect, the invention features treating a patient having a pathogenic cell disease with a conditioning regimen that retains a functional population of the patient's T lymphocytes. This second method also includes administering a preparation that includes allogeneic stem cells from a donor to the patient under conditions effective for inducing host anti-donor unresponsiveness. The regimen can be a M/- or a M/l conditioning regimen.

The method may also include a step of providing a regimen of allogeneic cell therapy to the patient following induction of the host anti-donor responsiveness and in the absence of significant GVHD. The conditioning regimen can include administration of an alkylating agent such as busulfan or cyclophosphamide. Cyclophosphamide can be administered together with hydroxyurea. Alternatively, the conditioning regimen can include administration of total body irradiation, preferably accompanied by administration of cyclophosphamide.

In another aspect, the invention features a method of making a patient-specific allogeneic stem cell preparation. The patient, having been administered a conditioning regimen, is endowed with a selected veto capacity. The method includes obtaining a stem cell preparation from an allogeneic donor and adjusting the veto capacity of the preparation to balance the selected veto capacity of the patient. The method may also include adjusting the veto capacity of the patient to balance the veto capacity of the preparation.

The term "myeloablative" as used herein includes any therapy that eliminates, through cell killing or cell inactivation, substantially all the hematopoietic stem cells of host origin. "Myeloablative" is herein referred to as "M".

The term "sub-myeloablative" as used herein includes any therapy that eliminates a significant fraction of, but not substantially all, hematopoietic stem cells of host origin. "Sub-myeloablative" is herein referred to as "m".

The term "lymphoablative" as used herein includes any therapy that eliminates substantially all functional T lymphocytes of host origin. This is accomplished through cell killing, blocking, and/or down-regulation. The elimination may be short-term or long-term. "Lymphoablative" is herein referred to as "L".

The term "sub-lymphoablative" as used herein includes any therapy that eliminates a significant fraction of, but not substantially all, functional T lymphocytes of host origin. "Sub-lymphoablative" is herein referred to as "l".

The terms M, m, L, and l can be combined in any fashion to categorize particular conditioning regimens. For example, the term "M/L," as described above, refers to a conditioning regimen that is myeloablative and lymphoablative. The term "m/L" refers to a conditioning regimen that is sub-myeloablative and lymphoablative. The terms "M/l" and "m/l" likewise refer to the corresponding conditioning regimens.

The term "-/L" as used herein refers to a conditioning regimen that is lymphoablative but that does not significantly affect the patient's hematopoietic stem cells.

The term "M/-" as used herein refers to a conditioning regimen that is myeloablative but that does not reduce the patient's T lymphocytes.

Graft versus pathogenic cell effect as used herein refers to response of the graft against any pathogenic cell including a cancer cell, genetically abnormal stem cell, self-reactive T lymphocyte as in an autoimmune disease, and an infected host-derived cell such as an HIV-1 infected T cell or reticuloendothelial cell.

The term "cancer" as used herein includes all pathological conditions involving malignant cells; this can include "solid" tumors arising in solid tissues or organs as well as hematopoietic tumors such as leukemias and lymphomas.

Major advantages are to be anticipated as a result of clinical application of the methods described herein, foremost being a relatively low incidence of short-term and long-term complications. Thus, patients should experience fewer episodes of infections, and are at reduced risk for bleeding due to thrombocytopenia, veno-occlusive disease of the liver, and interstitial pneumonitis. Patients treated with the disclosed methods also generally experience reduced rates of severe acute and chronic GVHD.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents and other references mentioned herein are incorporated by reference in their entirety. In case of conflict, the present specification, including definitions, will control. In addition, the materials, methods and examples are illustrative only and are not intended to be limiting.

Other features and advantages of the invention will be apparent from the following detailed description, and from the claims.

DETAILED DESCRIPTION

Figure 1A:
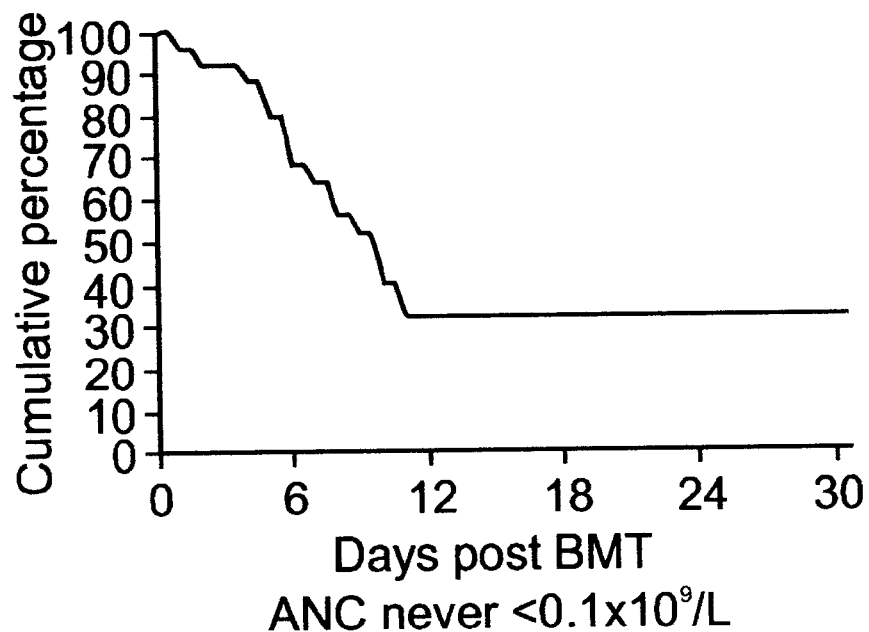
FIG. 1 is a series of plots showing duration and degree of pancytopenia and engraftment of HLA-identical G-CSF mobilized blood stem cell allografts following a m/L conditioning regimen.
Figure 1B:
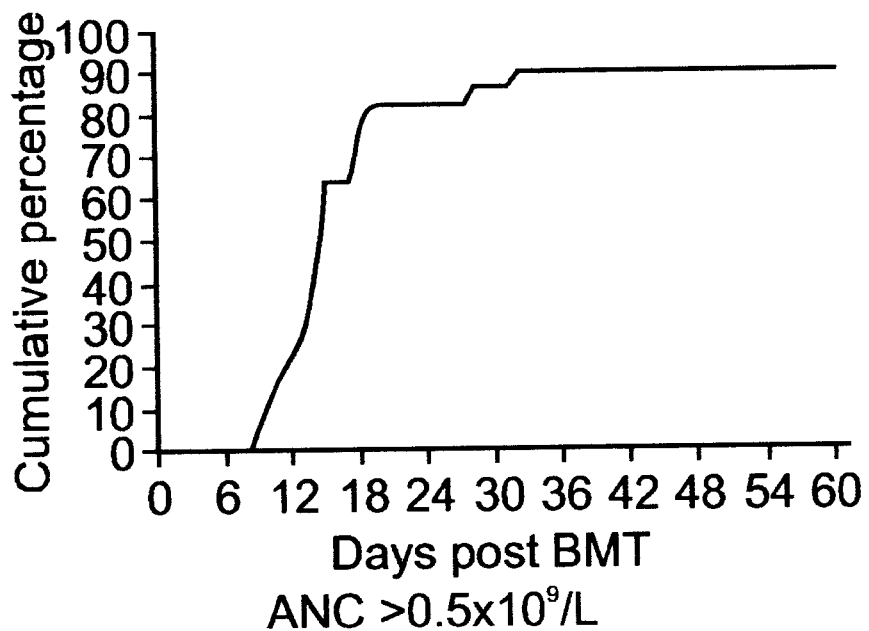
Figure 1C:
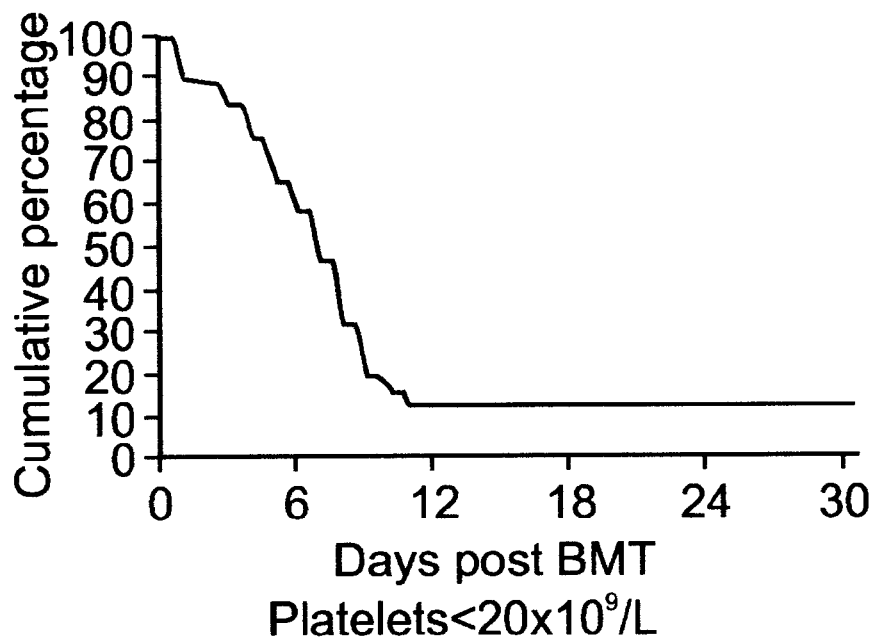
Figure 1D:
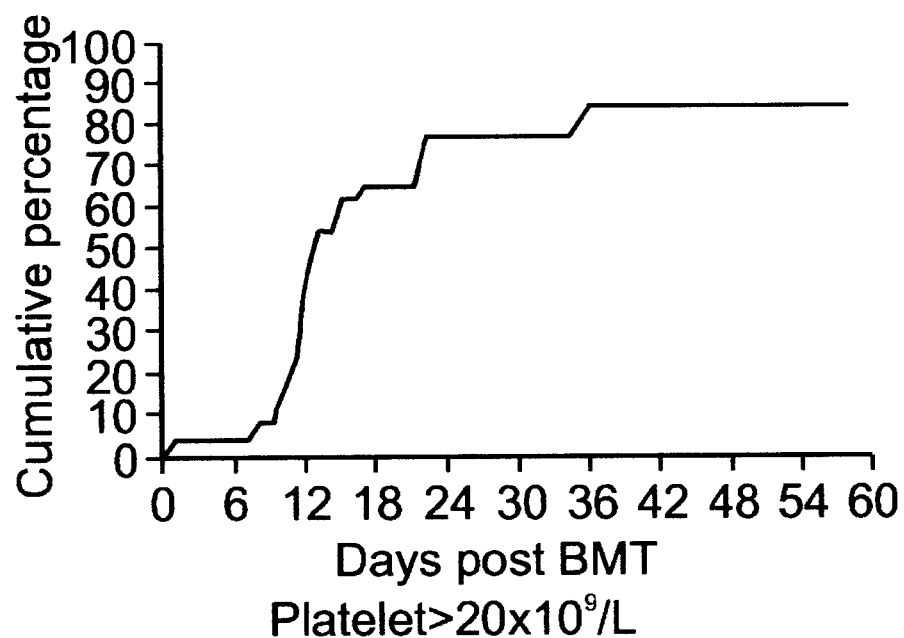

Two general approaches to conditioning regimens have been developed that circumvent the need to substantially eliminate both the patient's hematopoietic stem cells and T lymphocytes. In the first approach (Method 1), the patient is provided a lymphoablative conditioning regimen (-/L) or (m/L) that allows retention of a functional population of hematopoietic stem cells but that eliminates substantially all the patient's T lymphocytes. In the second approach (Method 2), the patient is provided a myeloablative conditioning regimen (M/-) or (M/l) that eliminates substantially all the patient's hematopoietic stem cells, but that allows retention of a functional population of the patient's T lymphocyte population.

After the patient is treated with one of the conditioning regimens described above, a donor-derived preparation that includes allogeneic stem cells is administered to the patient. The preparation is administered under conditions effective for inducing host anti-donor unresponsiveness. In an optional third step, the patient may be administered a regimen of allo-CT following induction of anti-donor responsiveness by the host and in the absence of significant GVHD.

Human patients with a variety of pathogenic cell diseases can be treated by the methods of the invention. Pathogenic cell diseases include malignant diseases such as chronic myelogenous leukemia (CML), acute myelogenous leukemia (AML), acute lymphoblastic leukemia, non-Hodgkin's lymphoma NHL), myelodysplastic syndrome (MDS), multiple myeloma (MM), primary central nervous system lymphoma (CNS lymphoma), as well as solid tumors such as metastatic breast cancer.

Pathogenic cell diseases also include non-malignant diseases, for example genetic disorders. Examples of non-malignant diseases include β-thalassemia major, Fanconi's anemia, Gaucher's disease, Blackfan Diamond syndrome, acquired immunodeficiency syndrome (AIDS), as well as autoimmune diseases.

METHOD 1

A human patient with a pathogenic cell disease is treated with a conditioning regimen that retains a functional population of the patient's hematopoietic stem cells. Retention of a functional stem cell population allows the patient to avoid commonly encountered clinical effects of cytopenia, for example sepsis and fungal infections due to neutropenia, susceptibility to life-threatening parasites such as *Pneumocystis carinii* and bleeding due to thrombocytopenia. Preferably, the patient retains at least about 20% of the functional hematopoietic stem cell population, more preferably at least about 50%, and most preferably at least about 90%, of the functional stem cell population.

With respect to the patient's hematopoietic stem cells, the conditioning regimen can be sub-myeloablative. Alternatively, the regimen may lack any conditioning that depletes the patient's functional hematopoietic stem cells, i.e. the regimen may allow for retention of substantially all the patient's functional hematopoietic stem cells.

With respect to the patient's functional T lymphocyte population, the conditioning regimen of Method 1 includes an intense lymphoablative regimen that transiently eliminates the patient's functional T lymphocyte population. The lymphoablative regimen may also transiently eliminate the natural killer (NK) cell population. This severe lymphoablation reduces or suppresses the functional T lymphocyte population to a level that allows engraftment of allogeneic donor cells in a large majority of patients subjected to the conditioning regimen. Preferably the lymphoablative regimen is sufficiently severe to allow allogeneic stem cell engraftment in at least about 90% of patients. More preferably, the lymphoablative regimen is sufficiently severe to allow allogeneic stem cell engraftment in nearly 100% of patients.

Preferably, the lymphoablative regimen transiently decreases the host functional T lymphocyte population by at least about 90%. More preferably, the lymphoablative regimen transiently decreases the host functional T lymphocyte population by at least 95%, and most preferably, by at least about 99%.

Thus, the conditioning regimens applicable to Method 1 can be classified as m/L or -/L conditioning regimens.

Examples of agents useful for sub-myeloablative components of the conditioning regimen include alkylating agents such as busulfan, cyclophosphamide, hydroxyurea, i.e., carmustine (BCNU), etoposide (VP16), chlorambucil, thiotepa, carboplatin, cisplatin and melphalan. Other agents may also be useful for sub-myeloablative conditioning such as cytosine arabinoside (ara-C) and anthracyclines such as idarubicin. Low-dose ionizing irradiation delivered by an exogenous radiation source such as cobalt or linear accelerator may also be used. An internal source can be used by providing a bone-seeking radiolabeled compound such as strontium or a radioactive compound targeted to stem cells by stem cell specific antibodies.

Examples of agents useful for lymphoablative components of the conditioning regimen include purine analogs such as methotrexate, cladribine (2-CDA) and fludarabine (FLU). Alkylating agents such cyclophosphamide also may be used for lymphoablative conditioning. Melphalan, thiotepa and busulfan are alkylating agents that are weakly immunosuppressive and may also be used. Polyclonal and monoclonal anti-leukocyte globulins such as anti-lymphocyte globulin (ALG), anti-thymocyte globulin, anti-T lymphocyte globulin (ATG) and antibodies against well-defined T lymphocyte subsets may also be used. Lymphoid irradiation may also be used.

Doses of agents that have both myeloablative and lymphoablative activities can be adjusted to provide the appropriate myeloablative, sub-myeloablative, lymphoablative, or sublymphoablative activities. This is illustrated, for example, in the patient protocols summarized below in the Examples. When an m/L conditioning regimen is used, a combination of alkylating agents, purine analogs and/or anti-leukocyte globulins can be used as conditioning agents. A preferred m/L conditioning regimen includes administration of sub-myeloablative amounts of busulfan, together with amounts of FLU plus ATG sufficient to accomplish severe lymphoablation. If the day on which stem cells are infused is set as day 0, then a typical conditioning regimen under Method 1 can be summarized as follows:

FLU: 30 mg/m$^2$/day for 6 consecutive days (days −10 to −5)

Busulfan: 4 mg/kg/day for two consecutive days (days −6 and −5)

ATG: 10 mg/kg/day for 4 consecutive days (days −4 to −1)

In an alternative embodiment, cyclophosphamide at 10–60 mg/kg/day for two consecutive days at days −6 and −5 can be substituted for busulfan. It is to be understood that these agents and dosing schedules are illustrative only, and that other agents and dosing schedules having similar effects on the patient can be employed.

When a -/L conditioning regimen is employed, agents administered may include alkylating agents and anti-leukocyte globulins. A preferred -/L conditioning regimen employs appropriate doses of cyclophosphamide and ATG to accomplish severe lymphoablation without significant myeloablation. For example, ATG can be provided at 10 mg/kg/day on days −8 to −5, and cyclophosphamide provided at 50 mg/kg for one, two, three or four consecutive days beginning on day −4. Two to four consecutive doses of cyclophosphamide are preferred in this case, since this leads to a greater likelihood of stem cell engraftment than if cyclophosphamide is limited to one dose. Again, it is to be understood that these agents and dosing schedules are illustrative only, and that other agents and dosing schedules having similar effects on the patient can be employed.

After the patient is treated with one of the above-described conditioning regimens, a donor-derived preparation that includes allogeneic stem cells is administered to the patient. The stem cell preparation may also include donor-derived T lymphocytes.

Although it may be desirable in many circumstances to use an HLA-compatible donor, in other cases it is permissible to have a mismatch at one or more histocompatibility loci. Thus, the donor may be a sibling matched at HLA-A, B, C, DR, DRB1 loci. In other embodiments, however, the donor may be one, two or three locus-mismatched with the patient at either class I, class II or both.

T lymphocytes in the donor-derived stem cell preparation, and to a lesser extent the stem cells themselves (see below), can act as "veto" cells to produce a veto effect. Veto cells as used herein include T lymphocytes, especially $CD8^+$ T lymphocytes, or other cells that result in down-regulation rather than stimulation of other T lymphocytes against cells containing the same alloantigens as the veto cells themselves. Other proliferating hematopoietic cells including T lymphocyte-depleted stem cells that are poorly immunogenic may also induce veto effects against T lymphocytes. In this context, most or all cells that bear cell surface alloantigens can serve as veto cells. The veto capacity of a cell may be transient. For example, the veto capacity of a cell may be higher during cell division than during quiescent periods.

Even with severe lymphoablation, there may be small numbers of residual lymphocytes in the patient. Furthermore, the residual lymphocytes can expand in number in response to alloantigens, leading to a host versus graft effect. Through the veto phenomenon, residual host T lymphocytes can be down-regulated by donor-derived veto cells, including stem cells and/or T lymphocytes. Other replicating donor-derived cells can also veto host-derived T lymphocytes if provided in relatively high concentrations. Conversely, immunocompetent T lymphocytes present in the donor preparation can be down-regulated by veto cells of host origin. Thus, a balanced equilibrium can be attained that minimizes or even eliminates graft versus host responses, thus minimizing or preventing possible GVHD. A balanced equilibrium can also minimize or eliminate host versus graft effects, thus reducing the chance of graft rejection.

A balanced equilibrium is accomplished by balancing the alloreactive T cells of the donor with the veto cells of host origin presenting the appropriate antigens (class I and/or class II antigens or other minor histocompatibility antigens in a non-immunogenic form). Likewise, alloreactive cells of the host may be balanced by veto cells of donor origin presenting the corresponding antigens (class I and/or class II antigens or other minor histocompatibility antigens in a non-immunogenic form). Adjustment of the veto capacity of host-derived cells presenting host antigens and donor-derived cells presenting donor antigens results in the bilateral unresponsive state that is induced spontaneously and consistently in stable mixed chimeras.

To achieve a balanced equilibrium of veto capacity, the veto capacity of the donor-derived stem cell preparation can be adjusted to correspond to the patient's conditioning regimen. As the intensity of the patient's conditioning regimen decreases, especially the lymphoablative component, a larger proportion of residual alloreactive cells capable of causing rejection remain. Thus, larger numbers of donor cells with relatively strong veto capacity are required. In the donor stem cell preparation, T cells and stem cells can down-regulate host alloreactive cells and prevent graft rejection, hence the need for higher numbers of donor cells as the host conditioning regimen decreases in intensity. The veto cells of the host likewise can prevent GVHD despite the inoculation of a larger number of alloreactive donor-derived T cells. This explains the requirement for an increased number of donor stem cells when the graft is T cell depleted, since the lack of T cells acting as veto cells must be compensated for by an increased number of stem cells. In this case, the stem cells provide the required proportions of tolerizing antigens in non-immunogenic form necessary for down-regulation of residual host alloreactive T cells.

Donor hematopoietic stem cells can be obtained by direct extraction from the bone marrow or from the peripheral circulation following mobilization from the bone marrow. The latter can be accomplished by treatment of the donor with granulocyte colony stimulating factor (G-CSF) or other appropriate factors that induce mobilization of stem cells from the bone marrow into the peripheral circulation. The mobilized stem cells can be collected from peripheral blood by any appropriate cell pheresis technique, for example through use of a commercially available blood collection device as exemplified by the CS3000 Plus blood cell collection device marketed by the Fenwal Division of Baxter Healthcare Corporation. Methods for performing apheresis with the CS 3000 Plus machine are described in Williams et al., *Bone Marrow Transplantation* 5: 129–133 (1990) and Hillyer et al., *Transfusion* 33: 316–321 (1993).

Alternative sources of stem cells include neonatal stem cells (e.g., cord blood stem cells) and fetal stem cells (e.g., fetal liver of yolk sac cells). Stem cells that have been expanded in vitro with a mixture of hematopoietic cytokines also may be used. Other useful stem cell preparations include stem cells that have been transduced with genes encoding donor-type MHC class I or class II molecules, as well as stem cell preparations containing stem cells and/or T cells transduced with herpes simplex thymidine kinase or other "suicide" genes to render the mature T cells sensitive to ganciclovir or other appropriate drugs in the event of severe GVHD. Similarly, donor or host derived T cells transduced with herpes simplex thymidine kinase or other "suicide" genes to render the mature T cells sensitive to ganciclovir or other appropriate drugs may be used for vetoing host or donor T cells, thus controlling for rejection or GVHD, respectively.

The hematopoietic stem cells in the preparation are administered under conditions effective for inducing donor-specific unresponsiveness by the host. Such unresponsiveness results when donor stem cells are able to engraft in the patient as the result of an appropriate conditioning regimen.

As described above, the donor-derived stem cell preparation can include donor T lymphocytes in addition to the hematopoietic stem cells. The preparation of donor hematopoietic stem cells can even be enriched for T lymphocytes, particularly if a relatively high veto capacity is needed to balance a robust residual population of T lymphocytes in the host patient. It is noteworthy that the T lymphocytes in the stem cell preparation can engender a graft versus pathogenic cell effect within the context of the donor-specific unresponsiveness resulting from engraftment of the donor hematopoietic stem cells.

In some embodiments, an anti-GVHD agent may be administered to the patient. Since an anti-GVHD agent suppresses T lymphocytes, it can also suppress the graft versus pathogenic cell effect and the veto capacity of the T lymphocytes. Therefore, it is advantageous to cease administration of the anti-GVHD agent as early as possible in order to facilitate the graft versus pathogenic cell effect as well as the veto capacity of the donor stem cell preparation.

The administration of the anti-GVHD agent may be gradually diminished when the patient shows signs of donor stem cell engraftment, provided that indications of GVHD are absent or negligible. Although the anti-GVHD agent can be administered for more than three months if necessary, preferably the anti-GVHD agent is administered to the patient for no more than about ninety days, even more preferably for no more than about thirty days. Cyclosporin A is a particularly useful anti-GVHD agent. Other agents effective to prevent GVHD are within the scope of the invention. Examples of other anti-GVHD agents include methotrexate, imuran, cellcept (mycophenolate mofetil), ALG, anti-lymphocyte function and anti-adhesion/homing antibodies, and corticosteroids.

Alternatively, an anti-GVHD agent may not be necessary if the veto capacity of the donor-derived preparation is adequately balanced by the veto capacity of the host patient. In such a case, since the veto cells of the donor are in balance with the host, they "veto" each other leading to substantial reduction or even total avoidance of GVHD. As discussed above, the veto capacities can be balanced by adjusting the veto capacity of the donor-derived preparation to correspond to the conditioning regimen of the patient, or vice versa. In situations of mixed chimeras, where donor- and host-derived hematopoietic cells coexist, the veto capacities may be inherently balanced.

The patient may be administered other compounds such as antibiotics, that can be administered prophylactically. For example, septrin, acyclovir and ganciclovir can be given prophylactically for pneumocistis carinii, herpes simplex virus and cytomegalovirus prevention, respectively, prior to administration of the donor-derived stem cell preparation.

Engraftment of donor stem cells in the host can be detected by any number of standard methods. The presence of donor markers, such as sex chromosome-specific markers, in the host can be determined, for example, using standard cytogenetic analysis, polymerase chain reaction (PCR) with appropriate primers, variable number of tandem repeats-PCR (VNTR-PCR), microsatelite markers or other finger-printing techniques, or fluorescence in situ hybridization (FISH). Host-donor chimerism can also be determined by determining the percentage of donor-type cells in host blood using, for example, standard complement-dependent microcytotoxicity tests.

After engraftment of donor-derived cells, the patient can be provided a regimen of allo-CT to supplement any graft versus pathogenic cell effects of donor lymphocytes infused with the stem cell preparation. Allo-CT is described, for example, in PCT Publication No's. WO 95/24910 and WO 96/37208. Allo-CT involves administering donor-derived allogeneic peripheral blood T lymphocytes to the host, either alone or in combination with a T cell activator such as interleukin-2 (IL-2). Preferably, the allogeneic peripheral blood T lymphocytes are given in graded increments to prevent or control GVHD. Allogeneic peripheral blood lymphocytes can be "pre-activated" in vitro using a T cell activator such as IL-2, then administered either alone or in combination with the same or different T cell activator. Alternatively, allogeneic peripheral blood lymphocytes engineered with a suicide gene, such as the herpes simplex virus thymidine kinase gene, can be given at an early stage post transplantation. T lymphocytes engineered in such a manner over a wide range of cell numbers, can be administered since such cells can be selectively eliminated later if necessary.

Preferably, one or more infusions of about $10^5$ to about $10^9$ cells/kg of allogeneic peripheral blood lymphocytes are administered. These lymphocytes can be administered as defined T cell subsets (e.g., $CD4^+$ or $CD8^+$ subsets) if desired. Various T-cell activators are appropriate including, without limitation, IL-1, IL-2, IL-3, IL-4, IL-5, IL-6, IL-7, IL-10, IL-12, IL-13, IFNα, IFNγ, TNFα, anti-CD3, anti-CD28, phytohemagglutinin, concanavalin-A and phorbol esters.

Generally, allo-CT is performed after a desired level of anti-donor unresponsiveness has been induced in the host, with the allo-CT functioning to generate or amplify the graft versus pathogenic cell effect. Additionally, allo-CT can increase the proportion of donor cells in the host by causing further displacement of host hematopoietic stem cells.

Allo-CT typically involves administration of donor T lymphocytes to the host, although allo-CT can also include administration of donor-derived natural killer (NK) cells. During allo-CT, GVHD often can be controlled without the use of anti-GVHD agents. Although the presence of engrafted donor stem cells in the patient establishes a level of donor unresponsiveness, it is nevertheless prudent to administer allo-CT in graded increments while monitoring for signs of GVHD. Allo-CT is typically discontinued when GVHD and/or graft versus pathogenic cell effects (e.g., GVT, GVL) are indicated.

The T lymphocytes used in allo-CT may be life-span limited. Life-span limited cells can be controlled so as to function only transiently in the host. Life-span limited T lymphocytes can be generated, for example, by transformation with "suicide" gene vectors. See, e.g., Bonine et al., *Science* 276:1719–1724 (1997). Such vectors typically render the lymphocytes selectively susceptible to particular chemical agents, such as ganciclovir in the case of donor T cells transduced with herpes simplex virus carrying the thymidine kinase gene.

METHOD 2

In an alternative method of treating a human patient with a pathogenic cell disease, a myeloablative (M/-) or (M/l) conditioning regimen may be used. These regimens substantially reduce the patient's functional hematopoietic stem cell population while retaining substantially all (M/-) or a substantial fraction (M/l) of the functional T lymphocyte population. As a consequence, a patient treated with an M/- or M/l conditioning regimen has a particularly high veto capacity mediated by residual T lymphocytes. Suitable myeloablative conditioning regimens can include administration of myeloablative doses of one or more of the myeloablative agents described above. A typical conditioning regimen under Method 2 can be summarized as follows:

Busulfan: 4 mg/kg/day for four consecutive days (days −4 to −1)

It is to be understood that the use of busulfan at this dosing schedule is illustrative only, and that other agents and dosing schedules having similar effects on the patient can be employed. Other conditioning regimens may involve melphalan (120–240 $mg/m^2$ in 1 or 2 divided doses), thiotepa (10 mg/kg in 1 or 2 divided doses), high dose hydroxyurea (3–6 g/day until myeloablation is accomplished) or other variations of myleran such as dimethyl-myleran. Dibromo-manitol (DBM) may also be substituted for busulfan.

With M/- or M/l conditioning regimens, preferably the patient retains at least about 20% of the functional T lymphocyte population, more preferably at least about 50% of the functional T lymphocyte population and most preferably at least about 90% of the functional T lymphocyte population.

Following the conditioning regimen, the patient is administered a donor-derived preparation that includes hematopoietic stem cells. The donor-derived preparation can be a preparation with a high veto capacity, e.g., the preparation can contain large numbers of T lymphocytes, since the patient treated with the M/- or M/l conditioning regimen has a high veto capacity. If desired, the donor-derived preparation can be enriched for T lymphocytes or soluble non-immunogenic antigens to down-regulate alloreactive cells of host origin. The T lymphocytes of the donor-derived preparation not only provide veto capacity that controls for graft rejection but also may generate a substantial graft versus pathogenic cell effect. As discussed above under Method 1, allo-CT may also be administered to the patient following induction of host anti-donor unresponsiveness and in the absence of significant GVHD.

In view of the defined conditioning regimens that are employed in Methods 1 and 2, it is possible to specifically tailor a donor hematopoietic stem cell preparation for a particular patient. As discussed above, such preparations can be considered to possess a "veto" capacity defined by the ability of cells in the preparation to veto the anti-donor activity of T lymphocytes in the host patient. T lymphocytes in the stem cell preparation possess a significantly higher veto activity compared to the stem cells. Nevertheless, it appears that stem cells do have a relatively weak, but not insignificant, veto activity. Host and donor immunocompetent T cells that possess the most effective veto capacity can also cause untowards rejection and GVHD; thus, their numbers must be carefully balanced. Purified stem cells are, however, relatively safe because their veto capacity is not associated with alloreactivity against the donor or the host, respectively.

Ideally, the veto capacity of the stem cell preparation is matched, or "in balance," with that of the host patient. This minimizes the risk of GVHD while maximizing the likelihood of stem cell engraftment. To accomplish this, the numbers of T lymphocytes or stem cells, or both, can be adjusted to correspond to the intensity of the lymphoablative portions of the conditioning regimens.

If the patient is severely lymphoablated as in Method 1, the stem cell preparation need not carry substantial numbers of T lymphocytes, and may even be completely T cell depleted. In some cases the host patient may possess small numbers of residual donor-reactive lymphocytes in spite of intense lymphoablative measures. In these cases it is possible to supply sufficient veto capacity even in a T cell-depleted stem cell preparation by infusing particularly large numbers of stem cells. Alternatively, relatively small numbers of donor T lymphocytes can be included in the stem cell preparation in order to ensure veto of the residual host T cells. In still other cases, T lymphocytes can be added to a stem cell preparation (T lymphocyte enrichment), particularly if the stem cell preparation originally had a low number of T lymphocytes, and provided the veto capacity of the stem cell preparation remains functionally balanced with the veto capacity of the patient.

Accordingly, donor stem cell preparations also can be tailored to the conditioning regimens of Method 2, where the patient retains a functional population of T lymphocytes. In these cases, the donor-derived stem cell preparation typically is adjusted to have a relatively high veto capacity, balancing with the high veto capacity of the host patient. This can be accomplished by including high numbers of purified stem cells, or stem cells enriched for T cells.

The methods described herein may be safely offered to patients in all age groups with low anticipated incidence of immediate and long-term complications that result commonly from conventional transplants when myeloablation is combined with lymphoablation (M/L). Malignancies and genetic diseases may be treated at an early stage of the disease, with no undue delays due to the concern of the treating physician for procedure-related toxicity resulting from conventional BMT involving a M/L conditioning regimen. Treatment at an early stage may also avoid the need for repeated courses of chemotherapy with cumulative toxicity over the years. Treatment at an early stage of a disease may increase the chance of complete eradication of all tumor cells, before drug resistance occurs, by an optimal conditioning regimen and early allogeneic cell therapy. In genetic diseases, early treatment may prevent irreversible multiorgan damage especially when the central nervous system (CNS) is at risk. Similarly, patients with autoimmune diseases may also be excellent candidates for allogeneic stem cell transplantation, because early treatment may prevent irreversible complications such as ankylosis in rheumatoid arthritis, permanent CNS and paralysis in multiple sclerosis, and other complications. In patients with acquired immunodeficiency syndrome, early stem cell transplantation with allo-CT can reconstitute the patient's immune system with donor derived immunocompetent lymphocytes, preventing life-threatening infections and preventing or treating secondary malignancies.

In younger individuals, the methods described herein, in contrast to the traditional M/L conditioning regimens, should not lead to growth retardation and may reduce the risk of infertility due to chemo-sensitive gonadal and testicular tissues, while avoiding additional endocrine abnormalities and late complications such as cataracts.

In elderly individuals, who normally may not be qualified for a standard stem cell transplant procedure because of unacceptably high rates of complications, the methods of the present invention permit a relatively safe procedure. The ability to apply innovative allo-CT approaches following relatively safe stem cell transplants using the conditioning regimens of Methods 1 or 2 is likely to convince treating physicians to consider using curative transplant procedures at early stages of disease, when the chance for cure may be relatively high and before the disease spreads irreversibly to multiple organs. Furthermore, effective treatment at an earlier stage of disease may prevent development of chemotherapy-resistant tumor cell clones, platelet resistance induced by sensitization from repeated administration of blood products, cumulative multi-organ toxicity, and development of resistant strains of infective agents through repeated courses of anti-microbial therapy with susceptibility to fatal bacterial and fungal infections. Therapy mediated by the methods of the present invention may result in a significant change in the overall success rate for disease-free survival, as well as improvements in the quality of life and cost effectiveness for future candidates of stem cell transplantation.

In the future, early application of similar approaches for induction of transplantation tolerance may prevent sensitization of candidates to organ allografts and more effective use of the limited supply of organ allografts that can always be harvested with donor stem cells from both living and cadaveric donors.

The present invention will be further described with reference to the following examples; however, it is to be understood that the present invention is not limited to such examples.

EXAMPLES

Example 1

Method 1: (m/L) Conditioning Regimen—Fludarabine/ATG-Based Protocols

Patients and Methods

A combination of FLU at 30 mg/m²×6 days, busulfan at 4 mg/kg×2 days, and ATG was given to 26 patients undergoing m/L conditioning prior to administration of allogeneic donor-derived G-CSF mobilized (10 μg/kg×5 days) peripheral blood stem cells obtained from fully HLA matched, or 1–2 locus mismatched related donors. Patient characteristics are described in Table 1. All of the patients would have been considered eligible candidates for a standard allo-SCT program.

TABLE 1

Patients Undergoing m/L Conditioning Regimen

| UPN | AGE | DIAGNOSIS | D → H |
|---|---|---|---|
| 1031 | 50 | CML/CP | M → M |
| 1052 | 51 | 2° AML 1st CR | M → F |
| 1053 | 56 | CML/CP | M → M |
| 1057 | 16 | β-thalassemia major | M → F |
| 1073 | 19 | AML 2nd CR | F → F |
| 1077 | 19 | AML 1st CR | M → F |
| 1080 | 12 | ALL 2nd CR | F → M |
| 1088 | 37 | NHL, chemotherapy resist. | M → M |
| 1093 | 26 | AML 1st CR | M → F |
| 1098 | 61 | NHL, chemotherapy resist. | F → M |
| 1099 | 41 | MDS | M → M |
| 1109 | 1 | AML 1st CR | M → F |
| 1111 | 51 | Multiple myeloma | F → M |
| 1114 | 10 | Fanconi's anemia | M → F |
| 1119 | 2 | JCML | M → M |
| 1123 | 31 | Blackfan Diamond Anemia | F → F |
| 1124 | 20 | AML 1st CR | M → F |
| 1131 | 34 | CML/AP | F → M |
| 1133 | 29 | AML 1st CR | F → M |
| 1135 | 33 | CML/CP | F → F |
| 1137 | 38 | CML/CP | M → M |
| 1140 | 3 | Gaucher's Disease | M → F |
| 1141 | 39 | AML 1st CR | M → M |
| 1143 | 36 | CML/CP | F → M |
| 1156 | 46 | ALL 1st CR | M → M |
| 1158 | 46 | CML/CP | M → M |

*Donor (brother) was incompatible at A and C loci, with positive MLR in the direction of host versus graft.

The patients included 6 with chronic myelogenous leukemia in chronic phase (CML/CP); 1 with CML in accelerated phase (CML/AP); 1 with Juvenile CML (JCML); 7 with acute myelogenous leukemia (AML) in 1st complete remission (CR) one of whom had secondary leukemia (AML, m5) 3 years after treatment for carcinoma of the ovary and 1 with AML in 2nd CR; 1 with acute lymphoblastic leukemia (ALL) in 1st CR and 1 in 2nd CR; 2 with non-Hodgkin's Lymphoma (NHL) resistant to front line chemotherapy; 1 with myelodysplastic syndrome (MDS) with excess blasts; and 1 with multiple myeloma (MM). The series also included 4 patients with non-malignant disorders including 1 child with severe beta thalassemia major; 1 child with Fanconi's anemia; 1 child with Gaucher's disease and 1 adult with Blackfan Diamond Syndrome (Table 1).

Patient ages ranged between 2 to 61 (median 31) years. Conditioning prior to infusion of allogeneic stem cells included an m/L conditioning regimen with 6 daily infusions of FLU (Schering AG) for 6 consecutive days (−10 to −5), with each infusion containing 30 mg/m² (in adults the dose was adjusted according to ideal body weight); oral busulfan 4 mg/kg/day for 2 consecutive days (days −6 & −5); and ATG (Fresenius) 10 mg/kg/day for 4 consecutive days (days −4 to −1). One patient (UPN 111 with Fanconi's Anemia) received cytoxan 10 mg/kg/day for 2 consecutive days (days −6 and −5) instead of busulfan. G-CSF mobilized blood stem cells were collected from the donor once after a 5-day administration of G-CSF at 10 mg/kg/day. HLA-A,B,C,DR, DRB1 matched siblings were used as donors, with one exception: UPN 1109 was grafted with A and C locus mismatches as indicated by positive mixed lymphocyte reaction in the direction of host versus donor. The total number of nucleated cells infused on day 0 ranged between 3.38–16.39 (mean 8.60)×10⁸/kg. Prophylaxis against GVHD included standard cyclosporin A (CSA) 1.5 mg/kg twice daily intravenously starting on day −1, switching to an oral dose of 3 mg/kg twice daily as soon as the patients were discharged, with early tapering off starting as soon as engraftment with no GVHD was confirmed (around 4–6 weeks) and the patient's condition stabilized. Prophylaxis against *Pneumocistis carinii* included trimethoprim/sulfamethoxazole (10 mg/kg/day trimethoprin) given pre-transplantation (days −10 to −1) and reduced to 7 mg/kg/day trimethoprim twice weekly as soon as the absolute neutrophil counts exceeded $0.75 \times 10^9/L$.

Statistical Evaluation: The Kaplan-Meier method was used to calculate the probability of disease-free survival as a function of time as well as for determining the time to recovery of hematopoietic reconstitution.

Results

The m/L conditioning regimen was better tolerated in all the recipients compared to the anticipated side effects following a standard M/L conditioning regimen. As can be seen in Table 2, grade 3 or grade 4 toxicity (World Health Organization criteria) was not observed in any of the recipients. Grade 2 mucosities were documented in only 2 cases. All of the patients maintained oral intake throughout the procedure with 8 (31%) patients never requiring any parenteral caloric supplements. Septic fever episodes were observed in 4 cases, whereas 22 patients experienced no evidence of severe culture-positive systemic infection. Severe veno-occlusive disease (VOD) of the liver was observed in only 2 cases while 11 patients developed mild to moderate manifestations of VOD and 13 patients showed no evidence of hepatic abnormality at all. No pulmonary toxicity was observed in any of the patients.

TABLE 2

Common Transplant Related Complications.

| Common Complications | Incidence |
|---|---|
| Mucosal (Mucositis ≥ grade 2) | 2/26 |
| Hepatic (Veno-Occlusive Disease) | |
| Mild | 9/26 |
| Moderate | 2/26 |
| Severe | 2/26 |
| Pulmonary | 0/26 |
| Sepsis with positive blood culture | 4/26 |
| Systemic toxicity with multi-organ failure | 0/26 |

Additional important clinical parameters following m/L conditioning are shown in Table 3 and in FIG. 1. In 9 patients (31%), absolute neutrophil count (ANC) did not decrease below $0.1 \times 10^9/L$ and for the entire group it took a median of 10 days for the ANC to drop below $0.1 \times 10^9/L$ (FIG. 1A). Two patients never experienced ANC<$0.5 \times 10^9/L$ (Table 3). The number of days with ANC<$0.1 \times 10^9/L$ in the remaining seventeen patients ranged between 0 to 20 with a median of 4 days. ANC>$0.5 \times 10^9/L$ was accomplished within 10–32 (median 15) days. (FIG. 1B) Platelet counts did not decrease below $20 \times 10^9/L$ in 4 patients (Table 3), therefore requiring no platelet support at all. Among the remaining twenty-two patients, a drop of platelet count below $20\times10^9$/L was observed after a median of 7 days, with 11% probability of remaining with a low (<$20\times10^9$/L) platelet count after day 11 (95% confidence interval of 3–27%) (FIG. 1C). Spontaneous platelet counts of>$20\times 10^9$/L were achieved within 0–35 (median 12) days. Unsupported platelet counts>$20\times10^9$/L was observed within 36 days in 85% of the patients (95% confidence interval 69–95%) (FIG. 1D).

TABLE 3

Clinical Parameters Following M/L Conditioning

| UPN | ANC 0.1 × $10^9$/L | PLT 20 × $10^9$/L | ANC 0.5 × $10^9$/L | PLT >20K[4] | Grade | Acute GVHD on CSA[5] | Acute GVHD off CSA[6] | Mixed Chimerism | Chronic GVHD | Relapse or Residual Disease | Outcome |
|---|---|---|---|---|---|---|---|---|---|---|---|
| 1031 | – | 4 | +15 | 22 | 1 | + | | + | + | | A&W |
| 1052 | – | | +14 | – | 2 | | + | | + | | A&W |
| 1053 | +11 | – | +19 | – | 1 | | + | + | + | | A&W |
| 1057 | +8 | +9 | +11 | +12 | 3 | | + | + | + | | A&W |
| 1073 | +6 | +8 | +15 | +12 | 2 | + | | | + | + | Relapse (allo-CT)[8] |
| 1077 | +10 | +10 | +15 | +13 | 0 | | | | | | A&W |
| 1080 | + | 11 | +18 | – | 0 | | | | | + | A&W (allo-CT)[9] |
| 1088 | +5 | +5 | +10 | +12 | 0 | | | | | | A&W |
| 1093 | +10 | +7 | +14 | +10 | 4 | | + | | | | Died of GVHD |
| 1098 | +5 | +6 | +11 | +11 | 0 | | | + | + | + | A&W (allo-CT)[10] |
| 1099 | +6 | +6 | +15 | +12 | 0 | | | | | | A&W |
| 1109[7] | +2 | 0 | +28 | +36 | 3 | + | | | + | | A&W |
| 1111 | – | – | +15 | – | 0 | | | | | | A&W |
| 1114 | 0 | +0 | +15 | +22 | 0 | | | + | | | A&W |
| 1119 | – | +5 | – | +22 | 4 | | + | + | + | | A&W |
| 1123 | +8 | +5 | +13 | +15 | 2 | + | | | + | | A&W |
| 1124 | +11 | +9 | +32 | +35 | 4 | | + | + | | | Died of GVHD |
| 1131 | – | +3 | – | +8 | +4 | | + | + | | | Died of GVHD |
| 1133 | +9 | +4 | +18 | +12 | 0 | | | | | | A&W |
| 1135 | – | +8 | +18 | +10 | 4 | | + | | | | Died of GVHD |
| 1137 | – | +9 | +12 | +13 | 0 | | | + | | + | A&W (allo-CT)[11] |
| 1140 | – | +8 | +9 | +17 | 0 | | | | | | A&W |
| 1141 | +7 | +7 | –14 | +15 | 0 | | | | | | A&W |
| 1143 | +10 | +7 | +18 | +11 | 0 | | | | | | A&W |
| 1156 | +4 | 0 | +13 | +13 | 0 | | | | | | A&W |
| 1158 | +6 | +8 | +10 | 0 | 0 | | | | | | A&W |

[1]First day when ANC dropped below 0.1 × $10^9$/L.
[2]First day when platelets dropped below 20 × $10^9$/L.
[3]First day when ANC rose above 0.5 × $10^9$/L.
[4]First day platelet count rose above 20 × $10^9$/L; transfusion independent.
[5]GVHD initiated when patient was on CSA therapy.
[6]GVHD initiated when patient was off CSA therapy.
[7]Donor was a single locus A and C mismatched sibling, with a positive one way host anti-donor mixed lymphocyte culture.
[8]Patient with hematologic relapse 8 months following m/L conditioning currently under remission induction with a combination of chemotherapy for tumor debulking and allo-CT, in parallel with development of grade 2 GVHD.
[9]Patient with overt hematologic relapse at 4 months following m/L conditioning successfully treated by a combination of chemotherapy for tumor debulking and allo-CT, in parallel with development of grade 2 GVHD, with no evidence of disease, with 100% donor-type (female) cells by cytogenetic analysis and no male cells by PCR.
[10]Male patient with tumor cells completely resistant to all chemotherapy at the time of admission. The patient had residual disease following m/L conditioning with marrow infiltration by lymphoma cells. The patient was successfully treated with allo-CT in parallel with development of grade 2 GVHD. Currently, there is no evidence of disease, with 100% donor-type (female) cells by cytogenetic analysis and no male cells by PCR.
[11]Patient with no hematologic evidence of disease treated with allo-CT for cytogenetic relapse with positive bcr-abl RT-PCR.

GVHD≧grade 1 was observed in 12 of 26 patients (Table 3). Severe GVHD (grade 3 & 4) was the single major complication, diagnosed in 6 cases (25%) and was the only cause of mortality in 4 patients, all of whom developed the first signs of disease while off CSA. Interestingly, acute GVHD developed in only 4 patients while on regular CSA maintenance therapy with only 1 patient developing grade 3 GVHD while on CSA (UPN 1109, currently alive and well). In 8 cases, initiation of GVHD was observed only following sudden discontinuation of CSA in an attempt to enhance engraftment or displace residual host cells that were documented by molecular or cytogenetic analysis. The 4 patients who died from severe GVHD account for the only losses observed out of the entire series, with an observation period exceeding one year (median 8 months). In one of the patients (UPN 1093) who died of grade 4 GVHD, signs of disease developed while she was off CSA with no access to adequate follow-up or further CSA treatment as she was at that time living in a foreign country. Her death, therefore, may not be considered a protocol failure. The second patient (UPN 1124) died of GVHD grade 4 that developed immediately following discontinuation of CSA and re-infusion on day +22 of a second inoculum of blood stem cells enriched with blood T cells given intentionally without CSA in an attempt to enhance delayed granulocyte engraftment. Subsequently, granulocyte counts increased within less than a week and reached ANC>$0.5\times10^9$/L on day +35, suggesting that stem cell top-up may have not been mandatory and may have even contributed to development of GVHD with fatal outcome. The third and fourth patients with CML (UPN 1131 & 1135) also developed grade 4 GVHD after sudden discontinuation of CSA. All the other 8 patients who developed GVHD, of which only 3 manifested>grade 2 GVHD, responded to standard prednisone treatment starting with 2 mg/kg with slow tapering off as clinically indicated.

No conclusive data can be given at this point to assess the total incidence of chronic GVHD in m/L conditioned patients due to the relatively short observation period ranging from several months to over one year. As can be seen in Table 3, chronic GVHD was diagnosed in 9 patients, in 2 of which (UPN 1073 & 1098) signs of GVHD appeared only after initiation of allo-CT.

Engraftment was documented in all patients by increasing blood counts as shown in Table 3, and by either amelogenin-PCR for sex-mismatched host-donors as described in Pugatsch et al., 17:273–275 (1996), or VNTR-PCR in sex-matched donor-recipient pairs. Nakamura et al. *Science* (1987) 235:1616–1622. In 9 of 26 evaluatable patients, a transient stage of mixed chimerism was confirmed by documenting minimal residual host cells by cytogenetic analysis, PCR or disease-specific RT-PCR (e.g., bcr-abl in CML), and subsequently CSA was rapidly discontinued.

Relapse was observed in 2 patients with acute leukemia (UPN 1073 & 1080) whereas rapidly progressive residual disease was observed in one patient with NHL totally resistant to chemotherapy (UPN 1098). Cytogenetic relapse with normal hematologic parameters was diagnosed in one patient with CML who developed no spontaneous GVHD even following discontinuation of CSA, and is now under allo-CT therapy (UPN 1137). Successful displacement of tumor cells by allo-CT was accomplished in 2 cases (UPN 1080 and 1098) while one patient is still under treatment and too early for evaluation (Table 3).

UPN 1080, a male recipient originally treated for ALL in 2nd CR, featured no GVHD following m/L conditioning and administration of a donor-derived stem cell preparation, developed overt hematologic relapse at 4 months with the tumor mass doubling within 1–2 days. The large tumor mass was successfully debulked using a combination of cytosine arabinoside at 3 g/m$^2$/day in 2 split doses for 4 days and a single dose of mitoxantron at 12 mg/m$^2$, followed by re-infusion of lymphocyte-enriched donor (female) blood stem cells with no CSA. Elimination of all detectable male cells was confirmed by PCR analysis in parallel with GVHD (grade 1–2) induced following donor lymphocyte infusion (DLI), with stable CR being maintained to date with no further treatment.

UPN 1098 is an elderly male patient with fully resistant NHL, with rapidly progressive malignant lymphoid infiltrate in the marrow and bone neuroglia. The patient displayed no spontaneous GVHD following m/L conditioning and administration of donor-derived preparation. Elimination of all disease manifestations was confirmed following allo-CT with DLI in parallel with disappearance of host/male DNA by PCR and resultant 100% female karyotype, in parallel with onset of mild acute GVHD grade 2 that evolved to mild limited chronic GVHD. Another patient (UPN 1073) with AML in 2nd CR relapsed 9 months following m/L conditioning and administration of donor-derived preparation. She is currently under combined treatment with chemotherapy and allo-CT but she is too early to be evaluated.

Figure 2:
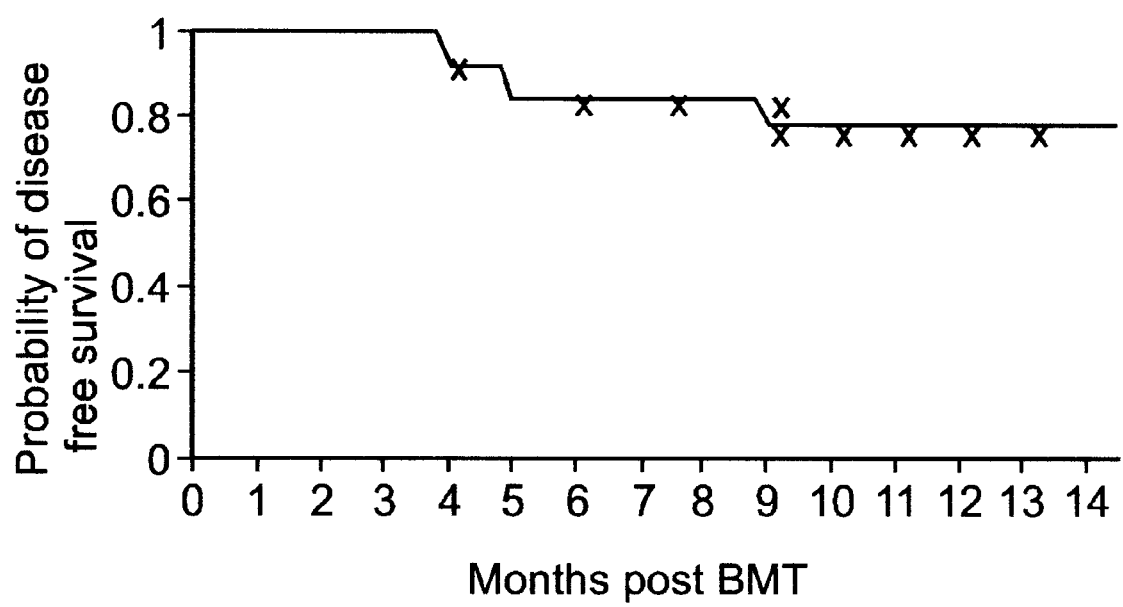
FIG. 2 is a plot showing the probability of disease free survival at various times post allo-SCT.

In an observation period extending over 1 year (median 8 months), 22 of 26 patients (85%) treated by allo-m/L conditioning and administration of donor-derived preparation are alive, 21 (81%) disease-free by all measurable criteria, including PCR, with excellent quality of life, and a Karnofsky score of 100%. The actuarial disease-free survival at a median follow-up of 8 months was 80.7% (at 14 months the actuarial disease-free survival was 77.5% with a 95% with a confidence interval of 53–90%) (FIG. 2). Mild and limited chronic GVHD developed in 9 of 25 patients with an observation period of >100 days, but thus far none have developed clinically significant manifestations.

Example 2

Method 1: (-/L) Conditioning Regimen—ATG/Cyclophosphamide-Based Protocols

Patients with various hematologic malignancies received a -/L conditioning regimen of ATG (Fresenius), 10 mg/kg/day on days -8 to -5, and cyclophosphamide at 50 mg/kg/day on days -4 to -1 or on days -2 to -1, followed by infusion of allogeneic peripheral blood stem cells (allo-PBSC) from matched related donors. All patients received cyclosporin A alone as GVHD prophylaxis. Patients and patient protocol details are provided below.

Results

Important clinical parameters and outcomes of patients treated with the -/L lymphoablative regimen are shown below in Table 4. Average time to ANC>$0.5\times10^9$/L was 13 days, while average time to platelets>than $20\times10^9$/L in 5/6 patients was 18 days (in UPN1050 the platelet count never decreased to below $20\times10^9$L). Two of the patients had clinical syndromes suggestive of venoocclusive disease, which resolved without sequelae (peak total bilirubin (TB) of UPN1042 peaked at 333 Mm/L, peak TB of UPN1056 peaked at 268 Mm/L).

Chimerism was analyzed for all patients with VNTR, and for patients with sex-mismatched donors by amelogenin (AMG-PCR). As shown in Table 4 below, all patients became chimeric, with no signs of rejection. Mild to moderate skin GVHD was present in 3/6 patients with liver and gut involvement in 3/6. UPN1003 died at 2 months post transplant with sepsis and GVHD of the gut, while UPN1042 died at 5 months after transplant with Staphylococcal pneumonia, relapsed NHL and moderate skin GVHD. It is worth noting that UPN0944 with Ph+ ALL, is in CR for over 11 months and UPN1026, with CNS lymphoma, is in CR for over 5 months. (See Example 3 below).

TABLE 4

| UPN# | age/sex | disease | conditioning | days to ANC > 0.5 | days to plt > 20 | VNTR | AMG-PCR | outcome |
|---|---|---|---|---|---|---|---|---|
| 0944 | 12M | Ph+ALL | ATG(4)/Cy(4) | 10 | 22 | donor | female | Allo-CT |
| 1003 | 50M | NHL | ATG(4)/Cy(4) | 11 | 13 | donor | NA | Died of GVHD |
| 1026 | 25F | CNS-NHL | ATG(4)/Cy(4) | 13 | 13 | donor | NA | Stem cells enriched with T-Cells |
| 1042 | 42F | MDS | ATG(4)/Cy(4) | 10 | 21 | donor | NA | Died of GVHD |
| 1050 | 54F | NHL | ATG(4)/Cy(4) | 18 | NA | donor | NA | A&W |
| 1056 | 50M | NHL | ATG(4)/Cy(4) | 14 | 22 | donor | female | Died of GVHD |

Additional patients conditioned with a (-/L) regimen are described below.

Patient 1

Diagnosis: Ovarian Cancer Stage lllc

A 49-year-old woman of good health came in for a routine physical exam. A pelvic mass was noted during the exam. Laparotomy was performed; total abdominal hysterectomy, oophorectomy, omentectomy and iliac node dissection was done as debulking, and the patient was surgically classified as minimal residual disease. Pathology showed poorly differentiated serous cystadenocarcinoma of ovary stage lllc.

Pre-operative CA-125 was 1,330, post-operative it dropped to 780. She then received 7 courses of cisplatinum/cytoxan which resulted in a drop of CA-125 to 26. Due to neurological changes, the patient was switched to carboplatinum/VP-16 for 4 cycles, but the CA-125 rose to 400. CT showed a new left iliac mass. A second laparotomy showed para-aortic node involvement with implants on the bladder, external iliac and obturator node involvement, which were debulked. With CA-125 at 600, she was treated with Taxol 175 mg/m². After 3 cycles, CA-125 dropped to 27, with CT showing no apparent disease. After 10 cycles of Taxol, CA-125 stayed at ~22 but CT showed a 2 cm mass under the diaphragm, without evidence of pelvic or nodal disease. Taxol was continued for a total of 28 courses, with a continued rise of CA-125 to 152.

While awaiting cell therapy, patient received several courses of cisplatinum 20 mg/d x3d q3w. CA-125 continued to rise with values of 328 and 439.6. On review of systems, the patient noted recurrent dysesthesias in the fingers, especially at night, similar to the symptoms present during the initial course of cisplatinum.

I. Conditioning:

The patient received ATG at 10 mg/kg/day on days −4 through −1, and cyclophosphamide at 50 mg/kg on day −1.

II. Donor Cell Infusion:

The patient received 7.79×10⁸ cells/kg G-CSF mobilized allo-PBSCT from her HLA-matched sister.

III. Engraftment:

The patient did not experience marked granulocytopenia. On day +4, the patient was discharged with a WBC of 3.4×10⁹/L for further follow-up as an outpatient. Engraftment can be followed with weekly RFLP to differentiate between donor engraftment and host recovery.

IV. Ovarian Carcinoma:

According to the plan, follow up of CA-125 was carried out as a marker of disease activity. On day +15, CA-125 was 280.

Patient 2

B.F. is a 36-year-old woman who was in a normal state of health when she noted a mass on her left breast. Although the initial biopsy was indeterminate, lumpectomy revealed invasive ductal carcinoma and a mastectomy was done. Lymph node biopsy showed 0/12 LN+ and no further therapy was given for this T1NONO ER positive tumor.

About 3½ years later, pectoralis muscle recurrence was detected and she was treated by resection followed by radiation therapy.

A year later, a new mass was noted on the right which was malignant with 7 out of 13 nodes positive. The mass itself was less than 2 cm. She was then treated with 6 cycles of CAF and 5000 cGyRT. Bone scan at the time showed a questionable T10 lesion. At 11 months, T10 collapsed, and by 8 months, the bone scan showed multiple bony involvement. She was then started on Taxol and Tamoxifen at 7 months which she received for 9 cycles, the last dose 5 weeks prior to admission. During this period she also developed hip pain that bone scan confirmed as being due to new metastases. The hip was treated with Spot RT and Tamoxifen was switched to MEGACE 3 months ago. Just prior to admission, head CT was within normal limits, chest CT showed tumor involvement in L3, bilateral iliacs and the sacrum. Abdominal CT showed that the organs were not involved with tumor. Bone marrow aspiration and biopsy were negative. Her entry CA 15-3, was 29 (WNL). Bone scan done on 20.6.95 (−16 days) showed new lesions in the posterior parietal skull on the right and rib 11 aside from the lesions present 26.2.95 (−5 months) in the left iliac wing, right femoral, vertebral column and ribs.

I. Conditioning:

ATG at 10 mg/kg/day IV, days −9 to −6; Cyclophosphamide at 50 mg/kg/day, days −5 to −2;

II. Transplant:

The patient received non T-cell depleted peripheral blood stem cells transplant (day 0) from her sister collected in two collections for a total of 5.22×10⁸ cells/kg.

III. GHVD prophylaxis:

On day −1 the patient was started on cyclosporin 2 mg/kg.

IV. Mucositis:

The patient had very mild oral mucositis during the neutropenic period.

V. Veno-occlusive disease of the liver (VOD):

The patient had a mild elevation in total bilirubin starting on day +6, reaching a high of 44 on day +10 and then returned to normal. There was never a significant rise in liver enzymes.

VI. Interstitial Pneumonitis (IP):

The patient was started on 1st protocol on day +6 without response. Amphotericin was added on day +10 and patient has been afebrile since.

VII. Engraftment:

On day +11, the patient had an ANC of 2×10⁹/L that was stable when the patient went off G-CSF until discharge.

VIII. GVHD:

On day +12, the patient developed marked skin rash, diarrhea, consistent with GVHD. Skin biopsy was consistent with GVHD. The patient was started on 2 mg/kg of steroids and continued on cyclosporin with good response of skin and gut. Skin rash was limited to the back. Bilirubin did not significantly rise from the time of onset of skin GVHD. The patient died of GVHD without any sign of the disease.

Patient 3

F.E. is a 57-year-old male, previously healthy who was diagnosed as having invasive gastric adenocarcinoma. CA-19-9:20. He has had psoriasis for a number of years. He underwent explorative laparotomy, and inoperative gastric cancer was found and partial resection was done. He was admitted for allogeneic PBSC transfer from an HLA-identical brother. After Hishman catheter insertion, small right-sided pneumothorax developed and had spontaneous resolution. Before admission a stent was inserted to the choledochus by ERCP. After the procedure the elevated bilirubin 100–120 mmol/L was normalized.

On CT he had isolated lung metastasis and abdominal was due to retroperitoneal gastric hepatic lymph nodes conglomerate. PE on admission pallor, no icterus, same psoriatic plaque on the skin and epigastric firm mass palpable.

Preconditioning:

ATG at 10 mg/kg/day×4 days iv; cyclophosphamide at a dose of 60 mg/kg/day×1 day.

On day 0, he received G-CSF mobilized PBSC from his HLA-identical brother to a total of $5.3 \times 10^8$ nucleated cells/kg.

After the procedure he was in good general condition. There was no sign of fever, bleeding, or any sign of infection and he was discharged.

Medication at home:

Oral Sucralent 1 gr×4

Oral Acyclovir 200 mg×3

Oral Respsin 2 grams/day twice weekly

The patient did not become chimeric and died of the disease.

Patient 4

A 16 month old baby (UPN 184) was found to suffer from β-thalassemia major when she was ten months of age. Treatment consisted of red blood cell transfusions. She underwent allogeneic BMT using her HLA matched MLC non-reactive grandmother as donor. There was major ABO mismatch ($A^+ \rightarrow O^+$). Pre-transplant conditioning included total lymphoid irradiation (TLI) 2 cGy×1/day×4 (total dose 8 Cgy), followed by busulfan 4 mg/kg/day×4 and cyclophosphamide 50 mg/kg/day×4. The transplant consisted of T-cell depleted marrow that had been treated in vitro with monoclonal rat anti-human Cdw52 (Campath 1M) with the donor's serum serving as source of complement. The protocol did not include post grafting immunosuppressive GVHD prophylaxis. Post BMT, the patient received 4 intravenous injections of donor peripheral blood lymphocytes in an attempt to prevent rejection and/or disease recurrence in doses equivalent to $10^3$ T cells/kg on day +1, $10^4$ T cells/kg on day +6, and $10^5$ T cells/kg on days +12 and +28.

The patient engrafted rapidly with absolute nucleated cells (ANC) reaching $0.5 \times 10^9$/l on day +19, $1.0 \times 10^9$ on day +27 and platelet counts of $\geq 2.5 \times 10^9$/l on day +29. On day +60 hemoglobin (Hb) level was 9.4 g/dl with no blood support and no evidence of ongoing hemolysis. Fourteen months post BMT the Hb levels dropped to 5.7–7.0 g/dl with MCV 70–72 (FL). Repeated assessment of donor-specific engraftment markers included blood group, semi-quantitative β-globin gene point mutation and PCR-VNTR tests. Whereas the PCR-VNTR test failed to demonstrate the presence of donor cells 24, 29, 45, and 51 months post BMT, the β-globin gene point mutation analysis detected 4–7% donor-derived DNA cells. The patient was homozygous for the mutation IVS -nt 110, and the donor was heterozygous for the same mutation. Blood group analysis constantly revealed the presence of donor red cells (type A). Notwithstanding the mixed chimeric-minimal donor cell state, the clinical picture presented as thalassemia intermedia-like with low transfusion requirement (8 transfusions over a 4-year period). Hb remained low (median 6.5 g/dl, range 5.4–7.0 g/dl), and serum ferritin levels rose from 437 to 700 μg/l. The patient displayed normal growth and development (percentile 50), although spleen size increased gradually to 4 cm below the left coastal margin and echo cardiogram showed disturbed left ventricle function.

To clarify the unusual clinical picture of this patient, a β-globin gene mutation assay was performed on cultured erythroid colonies, +/− erythropoietin (Epo). The addition of Epo resulted in propagation and differentiation of erythroid cells without nuclear expulsion. Donor cells without Epo amounted to 7%, similar to their percentage in peripheral blood lymphocytes and nucleated BMC, rising to 16% in the presence of Epo.

In view of the stable mixed chimerism, a second transplant was performed from the same donor, based on displacement of the host immunohematopoietic system without myeloablative conditioning. Pre-transplant ambulatory conditioning consisted of oral hydroxyurea (1,500 mg/day×6) followed by a single IV dose of 750 mg cyclophosphamide in parallel with IV mesna (250 mg×3).

On the day following the conditioning program, the patient received, on an ambulatory basis, unmanipulated G-CSF mobilized PBSC at a total number of $8.74 \times 10^8$/kg nucleated cells collected in three successive aphereses (Baxter CS 3000 plus) from the original donor. No post transplant immunosuppressive treatment was given. The patient tolerated the conditioning regimen extremely well, with no severe neutropenia or thrombocytopenia, and she therefore continued to be treated in the outpatient clinic. A dramatic spontaneous elevation in Hb level concomitant with a gradual increase in the percentage of donor-derived cells ensued. On day 52+ the patient suffered from signs of acute GVHD grade II, involving skin and intestine, for which she was treated with methylprednisone and cyclosporin A with good response. More than one year after the second procedure, the patient maintains an Hb count of 12.5 g/dl, and shows excellent clinical performance (Karnofsky score 100%). The donor-specific markers -β-globin gene point mutation, PCR-VNTR and blood group-analyzed in the peripheral blood and in BM aspirates, show 100% reconstitution with donor cells.

Patient 5

S.Z., a 31-year old woman, married with 4 children was admitted for allogeneic peripheral blood stem cell transplantation for metastatic breast cancer.

The patient had left breast cancer which was diagnosed during pregnancy. Bone scan revealed multiple metastasis. She was treated with combination chemotherapy-CAF with no response. She was getting hormonal therapy with Tamoxifen with no response and salvage chemotherapy with Taxol with no response. She was admitted for allogeneic peripheral stem cell transplantation from her fully-HLA-matched brother. Physical examination revealed poor general condition and large bilateral breast masses, huge left node on the left axilla, no hepatic enlargement.

Laboratory WBC 6500 with normal differentiation, hemoglobin 8.3 g/dl, platelets 350,000, biochemistry: Alkaline phosphatase 240 units and gamma GTP-387 units. CT scan showed multiple bone metastasis and bone marrow biopsy revealed malignant metastasis.

Conditioning for allo-transplantation included ATG 10 mg/kg/day×4 days and cyclophosphamide 50 mg/kg/day×4 days.

Allogeneic peripheral blood stem cell transplantation was performed with 3.87×10⁸ cells/kg.

GVHD Prophylaxis:

The patient received cyclosporin A from day −1 intravenously at doses of 3 mg/kg per day.

Post-transplant course:

The patient developed pancytopenia. She was transfused with red blood cells and platelets and received total parenteral nutrition (TPN). She had a temperature with negative blood cultures. She received a combination of antibiotic therapy. She developed mild veno-occlusive disease of the liver with maximal bilirubin of 30.

Engraftment:

On day +14, granulocytes appeared in the peripheral blood and then she had reconstitution of the white cells and platelets. She was discharged on day +20 post-transplant. In the outpatient clinic, the patient developed acute GVHD with involvement of the skin, liver and intestines. She proceeded with steroids with no response. She deteriorated rapidly with grade IV GVHD. She was hospitalized in another hospital, treated with a combination of cyclosporin steroids and antibiotics. She developed an infection and died from acute GVHD and its complications.

Patient 6

G.S. is a 50-year-old woman. She had a skin malignant melanoma over the shoulder that was removed and she received no further therapy. Three years later, a mass in the left axilla was found. She had wide excision of the mass including axillary lymph node and nuchal lymph node. Following surgery, she was treated with local radiation of 8,000 rads.

The patient was treated with cyclophosphamide and allogeneic lymphocytes plus IL-2 without evidence of engraftment and no signs of GVHD. The disease continued to progress. A mass from the urinary bladder was removed and last body CT showed lymphadenopathy in the right neck and retroperitoneal lymphadenopathy and lymph node in the right pelvis. Because of progression of the disease, it was decided to admit the patient for allogeneic peripheral blood stem cell transplantation.

Physical examinations revealed good general conditions. A small mass in the right neck 2 cm. No hepatosplenomegaly.

Laboratory:

Normal complete blood count. Normal biochemistry. All body CT scan showed lymphadenopathy in the peritoneum in pelvis and the mass in the neck.

Conditioning:

ATG at 10 mg/kg/day×4 days followed by cyclophosphamide at 50 mg/kg/day×4.

Allogeneic peripheral blood stem cell transplantation was performed by administration of 7×10⁸ cells/kg after mobilization with G-CSF.

Post-transplant course:

The patient had pancytopenia. She received red blood cells and platelet transfusions. On day +5, she had one episode of fever with positive blood culture with acinetobacter, sensitive to the antibiotic protocol that she received since the fever started.

GVHD prophylaxis:

The patient received cyclosporin A since day −1 intravenously at 3 mg/kg/day.

Engraftment:

On day +8 the first neutrophils appeared in the smear. Consequently, the patient had engrafted complete engraftment with normal white cell and platelet count. The patient was discharged on day +11 and currently she is without signs of GVHD, being treated with cyclosporin A at 7.5 mg/kg/day orally. The patient is under close follow-up in the outpatient clinic.

The patient showed transient engraftment because of the allo-CT prior to allo-PBSCT. The allo-CT sensitized the patient to the donor. Because the patient was transiently engrafted, the tumor regressed. However, the graft was eventually rejected and the tumor returned.

Example 3

Treatment of CNS Lymphoma With -/L Conditioning Regimens and PBSCT

A 25 year old woman was diagnosed as having primary central nervous system non-Hodgkin's lymphoma of the diffuse large B cell type after she had been suffering from nausea, vomiting and vertigo for 4 months. On computerized tomography (CT) and magnetic resonance imaging (MRI) a right cerebellar mass measuring 4 cm in diameter was visualized. Gross total resection of the mass was performed and the histopathological evaluation revealed a brain lymphoma. Systemic work-up, including whole-body CT (excluding the brain), abdominal ultrasound, bone marrow biopsy, bone scan, and repeated cerebrospinal fluid examinations showed no signs of lymphoma, confirming the diagnosis of PCNSL.

Post surgical chemotherapy included 2 bi-weekly courses of high-dose methotrexate (MTX, 3.5 g/m²) plus leucovorin rescue, and procarbazine (150 mg/m²/day) given for 14 days every 4 weeks. Due to liver dysfunction, procarbazine was discontinued and substituted by 1-(chloroethyl)-3 cyclohexyl-1-nitrosourea (CCNU, 100 mg/m²) for additional 6 cycles. In parallel, intraventricular injections of ARA-C (50 mg once every 2 weeks) were administered. Immediately following this, the patient received cranial irradiation (4500 Cgy) delivered to the whole brain and a boost of 1080 Cgy delivered to the tumor bed. Prior to irradiation and at completion of the radiotherapy, repeat MRI studies showed no evidence of disease. However, 2 months later, a routine follow up MRI evaluation showed a new mass in the posterior left lateral aspect of the medulla oblongata, which enlarged on subsequent imaging. The patient experienced sensory loss related to the distribution of the left first and second branches of the trigeminal nerve. Systemic chemotherapy consisting of 6 cycles of CCNU (100 mg/m²×1) and etoposide (50 mg/day×14) was administered. Then, high-dose MTX (2 cycles of 3.5 mg/m²) plus leucovorin rescue, and cisplatinum (40 mg/m²/day×3) were given followed by continuous high-dose ARA-C (1 g/m²/day×4).

Upon completion of the latter course of chemotherapy, MRI showed no resolution of the brain stem mass. Salvage treatment with high-dose chemotherapy followed by autologous BMT was judged ineffective in view of the chemoresistant disease in this patient.

Allo-BMT using her HLA-identical sister as donor was therefore implemented. Pre-transplant conditioning consisted of rabbit anti-human thymocyte globulin (ATG-Fresenius S, Bad Homburg, Germany, 10 mg/kg/day) from day −8 to day −5 and cyclophosphamide (50 mg/kg/day) from day −4 to day −1. IV CSA (3 mg/kg/day) was administered from day −1 as the only GVHD prophylactic drug. The patient received allogeneic peripheral blood stem cells (2.4×10⁶ CD34⁺ cells/kg out of a total number 5.5×10⁸ nucleated cells/kg) mobilized by subcutaneous injections of G-CSF 10 μg/kg/day×5 days). Engraftment was documented on day +12, with a white blood cell count of 1×10⁹/L and granulocyte count of >0.5×10⁹/L. From day +13 platelet count was above 25×10⁹/L.

The post transplant course was uneventful until day +10 when the patient developed acute grade II GVHD involving the skin as manifested by a maculopapular rash (confirmed by skin biopsy) and the liver as determined by mildly elevated total bilirubin and lactate dehydrogenase (LDH). On day +12 methylprednisolone (IV, 2 mg/kg) was added to the cyclosporin. By day +18, the skin rash had subsided and the liver function had started to normalize. After resolution of the GVHD, steroids and cyclosporin were tapered off and completely withdrawn at 3 months post transplantation.

Chimerism studies were based solely on DNA analysis of variable number of tandem repeat (VNTR) markers, since donor and recipients were of the same gender and shared the same blood group. On day +18, VNTR analysis revealed only donor-derived hematopoietic cells. The MRI examination performed at the same time showed marked shrinkage of the left medullary enhancing mass, and 3 months after the transplant the tumor was no longer discernible. To date, 13 months after the allogeneic stem cell transplantation the patient is in good clinical condition (100% Karnofsky performance status) without any sign of GVHD or lymphoma, demonstrating full donor cell chimerism.

The gradual manner in which the tumor resolved is comparable to the slowly achieved graft versus leucemia cell associated remission reported in chronic myeloid leukemia patients after BMT. The anti-lymphoma effect was associated with only moderate acute GVHD which responded to glucocorticoid and CSA treatment without abrogation of the anti-tumor effect. Thirteen months after the allo-PBSCT, the patient is in complete remission, showing full donor-derived hematopoiesis after resolution of the GVHD.

Example 4
Method 2: (M/l) Conditioning Regimens

Two patients received a M/l conditioning regimen. Patient 1 was a 24 year old male with CML in accelerated phase. He was admitted for allogeneic BMT. Conditioning was based on myeloablation with dibromomanitol (DBM) of 40 mg/kg on days −9 to −7 and cytosine arabinoside (ARAc) 20 mg/kg on days −6 to −4. The patient was weakly immunosuppressed with cytoxan 50 mg/kg on days −3 to −1. The patient received no radiation at all and no anti-lymphocyte globulin. The patient received non-T cell depleted G-CSF mobilized stem cells ($9.8 \times 10^8$ cells/kg) from his sister. The procedure was uneventful and mixed chimerism was confirmed by karyotypic analysis. No GVHD was observed at any stage. Perhaps due to lack of graft anti-host reactivity on the one hand and the advanced stage of the disease on the other, the Ph clone did not disappear and eventually full relapse was observed. The patient responded to a combination of cyclophosphamide (60 mg/kg for 2 days) and TBI 200 cGy×6 (total dose 1200 cGy) conditioning followed by a allogeneic stem cell transplantation and is now fully engrafted with 100% female cells and negative bcr/abl by reverse transcriptase-PCR.

Patient 2 was a 11 year old girl, who was 2 years old when first treated with BMT. She was diagnosed with β-Thalassemia major, treated with BMT and then relapsed. She received pretransplant ambulatory conditioning of hydroxyurea 1500 mg/day for 6 days (myeloablation) followed by a single low dose of cyclophosphamide (750 mg) in parallel with intravenous mesna (250 mg×3 for 1 day) for protection of the urinary bladder. On the day following cyclophosphamide, the patient received on an ambulatory basis, unmanipulated G-CSF (10 μg/kg for 5 days subcutaneously) mobilized blood stem cells at a total number of $8.74 \times 10^8$ nucleated cells/kg collected in three successive aphereses (Baxter CS 3000 plus) from the original donor (grandmother). The patient eliminated residual host cells (majority of cells, consisting of 95% of the DNA) so that the patient converted to 100% host and is now about four years out without any evidence of thalassemia or residual host cells.

Other Embodiments

Although the invention has been described with reference to the presently preferred embodiments, it should be understood that various modifications can be made without departing from the spirit of the invention. Other embodiments are within the following claims.

What is claimed is:

1. A method of inducing patient anti-donor unresponsiveness in a patient undergoing stem cell transplantation by subjecting the patient to a non-myeloablative/lymphoablative (-/L) conditioning regimen comprising the following steps:
   (i) treating the patient with a compound that is lymphoablative (L) and eliminates substantially all functioning T lymphocytes of patient origin while allowing the patient to retain a functional population of hematopoietic stem cells;
   (ii) administering a donor-derived preparation of allogeneic stem cells to said patient;
wherein said conditioning regimen results in patient donor-specific unresponsiveness and survival of the transplant.

2. The method of claim 1, wherein said stem cell preparation is obtained from bone marrow of said donor.

3. The method of claim 1, wherein said donor is a neonate.

4. The method of claim 1, wherein the stem cell preparation is obtained from cord blood of said neonate.

5. The method of claim 4, wherein the stem cell preparation is obtained from cord blood of said neonate.

6. The method of claim 1, wherein said donor is a fetus.

7. The method of claim 6, wherein the stem cell preparation is obtained from fetal liver of said fetus.

8. The method of claim 6, wherein the stem cell preparation is obtained from yolk sac of said fetus.

9. The method of claim 1, wherein the stem cell preparation is enriched for hematopoietic stem cells.

10. The method of claim 3, wherein, prior to obtaining the stem cell preparation from the allogeneic donor, a factor that mobilizes stem cells from the bone marrow into the peripheral blood circulation is administered to said donor.

11. The method of claim 10, wherein the factor is granulocyte colony stimulating factor.

12. The method of claim 9, wherein an increase in number of hematopoietic stem cells is achieved by contacting the preparation of hematopoietic stem cells is achieved by contacting the preparation of hematopoietic stem cells with a mixture of hematopoietic cytokines in vitro.

13. The method of claim 1, wherein said stem cell preparation comprises T cells.

14. The method of claim 13, wherein said T cells are CD8+ T cells.

15. The method of claim 13, wherein said stem cell preparation is enriched for T cells.

16. The method of claim 1, wherein said stem cell preparation is depleted of T cells.

17. The method of claim 1, wherein said donor is HLA-compatible with said patient.

18. The method of claim 1, wherein said donor is mismatched at one or more HLA class I loci, one or more HLA class II loci, or both one or more HLA class I loci and one or more HLA class II loci.

19. The method of claim 1, wherein said stem cell preparation comprises proliferating hematopoietic cells.

20. The method of claim 1, wherein stem cells, T cells, or both stem cells in the preparation are transduced with a suicide gene.

21. The method of claim 20, wherein the suicide gene is a herpes simplex thymidine kinase gene.

22. The method of claim 1, wherein the conditioning regimen comprises administration of one or more agents selected from the group consisting of purine analogs, alkylating agents, and anti-leukocyte globulins.

23. The method of claim 22, wherein the purine analog is fludarabine and the antileukocyte globulin is anti-T lymphocyte globulin.

24. The method of claim 1, wherein the conditioning regimen comprises administration of fludarabine, anti-T lymphocyte globulin and an alkylating agent.

25. The method of claim 24, wherein said alkylating agent is busulfan.

26. The method of claim 25, wherein the alkylating agent is cyclophosphamide.

27. A method of inducing patient anti-donor unresponsiveness in a patient undergoing stem cell transplantation by subjecting the patient to a non-myeloablative/lymphoablative (-/L) conditioning regimen comprising the following steps:

i) administering in the patient anti-T lymphocyte globulin at 10 mg/kg/day for 3 consecutive days at days −9 to −5;

ii) administering to the patient 50 mg/kg/day cyclophosphamide at days −4 to −1;

iii) administering a donor-derived preparation of allogeneic stem cells to said patient;

wherein said conditioning regimen results in patient donor-specific unresponsiveness and survival of the transplant.

* * * * *